United States Patent
Kadlub et al.

(10) Patent No.: US 12,336,737 B2
(45) Date of Patent: Jun. 24, 2025

(54) ACTIVATION TOOL FOR A BONE EXPANSION APPARATUS

(71) Applicants: ECOLE NATIONALE SUPERIEURE DE TECHNIQUES AVANCEES, Palaiseau (FR); ASSISTANCE PUBLIQUE HOPITAUX DE PARIS, Paris (FR); UNIVERSITÉ DE PARIS, Paris (FR)

(72) Inventors: Natacha Kadlub, Paris (FR); Jean Boisson, Paris (FR); Jérémy Dallard, Joinville le Pont (FR); Nicolas Kogane, Paris (FR)

(73) Assignees: ECOLE NATIONALE SUPERIEURE DE TECHNIQUES AVANCEES, Palaiseau (FR); ASSISTANCE PUBLIQUE HOPITAUX DE PARIS, Paris (FR); UNIVERSITÉ DE PARIS, Paris (FR)

( * ) Notice: Subject to any disclaimer, the term of this patent is extended or adjusted under 35 U.S.C. 154(b) by 438 days.

(21) Appl. No.: 17/597,415

(22) PCT Filed: Jul. 3, 2020

(86) PCT No.: PCT/EP2020/068900
§ 371 (c)(1),
(2) Date: Jan. 5, 2022

(87) PCT Pub. No.: WO2021/004972
PCT Pub. Date: Jan. 14, 2021

(65) Prior Publication Data
US 2022/0280196 A1    Sep. 8, 2022

(30) Foreign Application Priority Data
Jul. 5, 2019 (FR) .................................. 1907567

(51) Int. Cl.
| A61B 17/66 | (2006.01) |
| A61B 17/68 | (2006.01) |
| A61B 17/70 | (2006.01) |

(52) U.S. Cl.
CPC ........ *A61B 17/663* (2013.01); *A61B 17/7016* (2013.01); *A61B 2017/681* (2013.01)

(58) Field of Classification Search
CPC .............. A61B 17/663; A61B 17/8004; A61B 17/8009; A61B 17/8014; A61B 17/8019;
(Continued)

(56) References Cited

U.S. PATENT DOCUMENTS 4,947,853 A * 8/1990 Hon ..................... A61B 5/6843
                                                            600/459
5,070,880 A * 12/1991 Gomez ................ A61B 8/4236
                                                            600/455
(Continued)

FOREIGN PATENT DOCUMENTS

| EP | 1272115 A1 | 1/2003 |
| EP | 3061614 A1 | 8/2016 |
(Continued)

*Primary Examiner* — Eduardo C Robert
*Assistant Examiner* — Anna V. Little
(74) *Attorney, Agent, or Firm* — McNees Wallace & Nurick LLC

(57) ABSTRACT

The invention relates to an activation tool (1) for a bone expansion apparatus (3), the bone expansion apparatus (3) being a distraction plate apparatus (3), the activation tool (1) comprising a magnetic element (130) solidly attached to a rotation shaft (120) of the activation tool (1), the magnetic element (130) being configured to interact coaxially with a distant magnetic element (310) borne by the bone expansion apparatus (3), the activation tool (1) being characterised in that it further comprises an electric motor (110) configured to cause the rotation shaft (120) to rotate, and a control module (140) controlling the rotation of the rotation shaft (120).

(Continued)

The invention also relates to an assembly of a bone expansion apparatus (3) and of such an activation tool (1), in which the bone expansion apparatus (3) is a distraction plate apparatus (3).

9 Claims, 9 Drawing Sheets

(58) Field of Classification Search
CPC .......... A61B 2017/681; A61B 17/7016; A61B 17/66; A61B 17/80; A61B 5/150748; A61B 8/4236; A61B 8/4227; A61B 8/4209; A61B 8/42; A61F 2002/4687
See application file for complete search history.

(56) References Cited

U.S. PATENT DOCUMENTS

| | | | | |
|---|---|---|---|---|
| 5,211,160 | A * | 5/1993 | Talish | A61B 8/4227 607/51 |
| 2004/0030395 | A1 * | 2/2004 | Blunn | A61B 17/7016 623/23.45 |
| 2007/0173837 | A1 * | 7/2007 | Chan | A61B 17/66 606/63 |
| 2009/0112263 | A1 * | 4/2009 | Pool | A61B 17/707 600/587 |
| 2014/0031870 | A1 * | 1/2014 | Chang | A61B 17/705 606/264 |
| 2014/0128868 | A1 * | 5/2014 | Harrison | A61B 17/8004 606/60 |
| 2015/0313745 | A1 * | 11/2015 | Cheng | A61B 17/7216 602/19 |
| 2016/0296205 | A1 * | 10/2016 | Hays | A61B 46/23 |

FOREIGN PATENT DOCUMENTS

| | | | | |
|---|---|---|---|---|
| WO | 0178614 | A1 | 10/2001 | |
| WO | WO-2008003952 | A1 * | 1/2008 | ......... A61B 17/8004 |
| WO | 2015168175 | A1 | 11/2015 | |
| WO | WO-2017097998 | A1 * | 6/2017 | ............ A61B 17/66 |
| WO | WO-2018165243 | A1 * | 9/2018 | ........... A61B 17/663 |

\* cited by examiner

[Fig. 1]
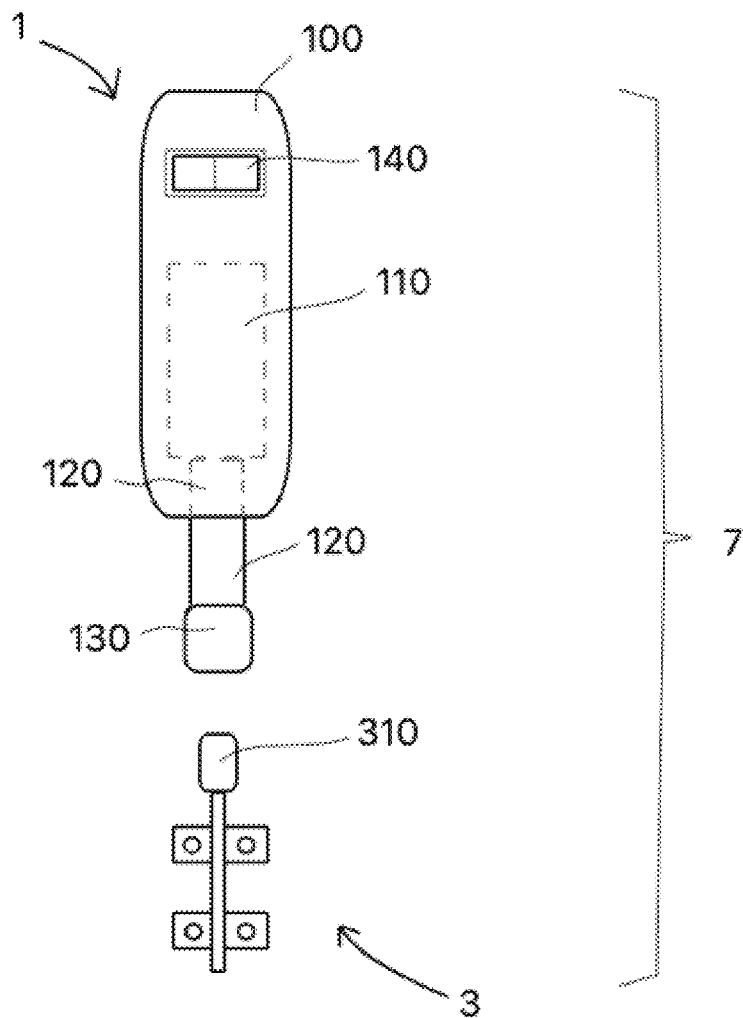
[Fig. 2]
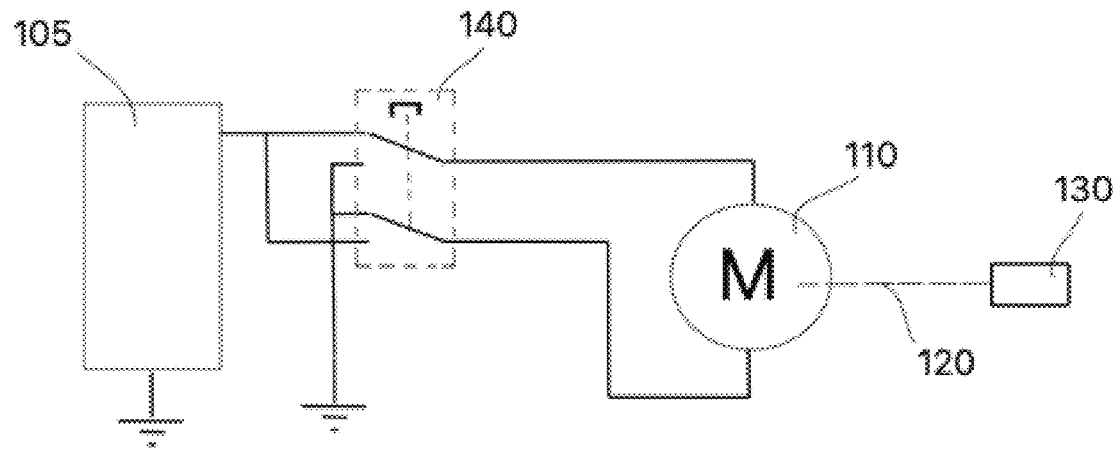

[Fig. 3]
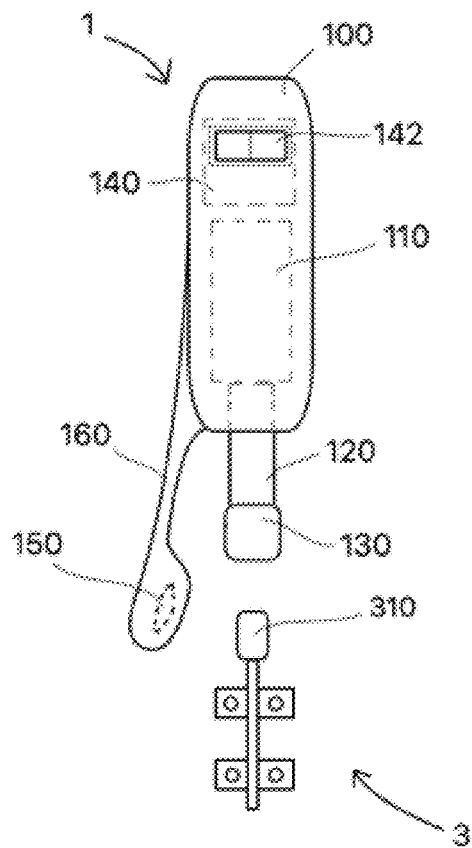
[Fig. 4]
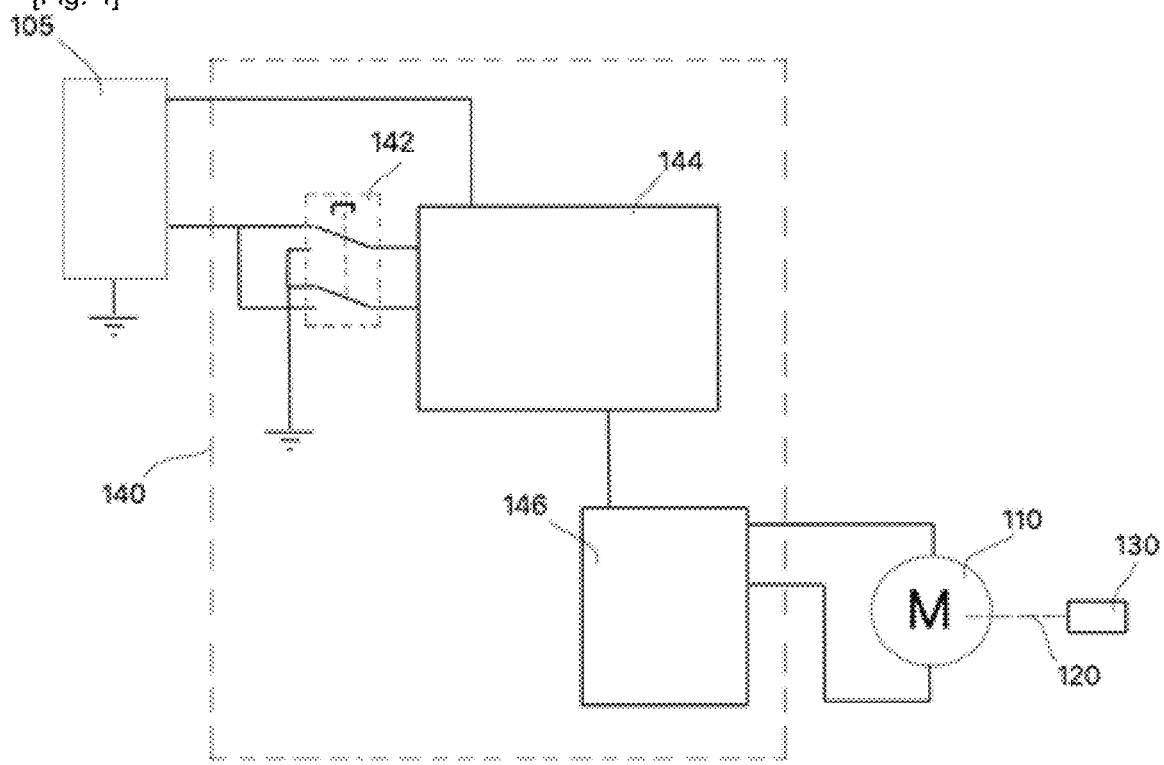

[Fig. 5]
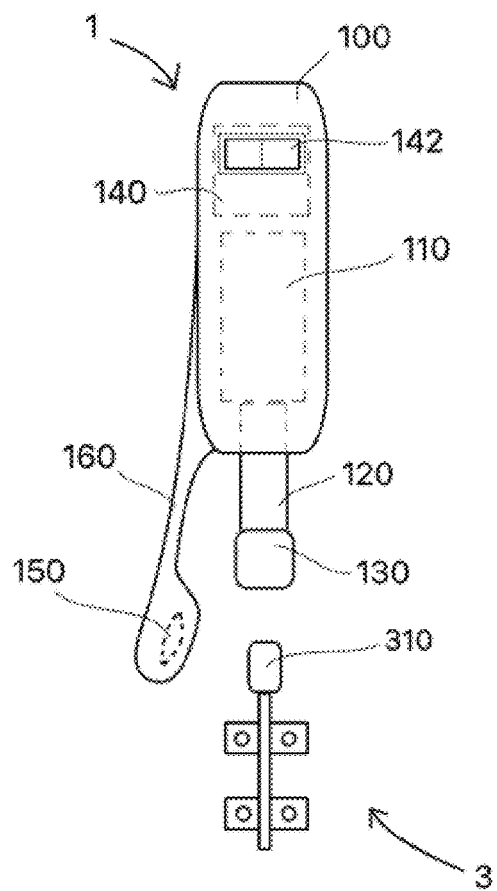
[Fig. 6]
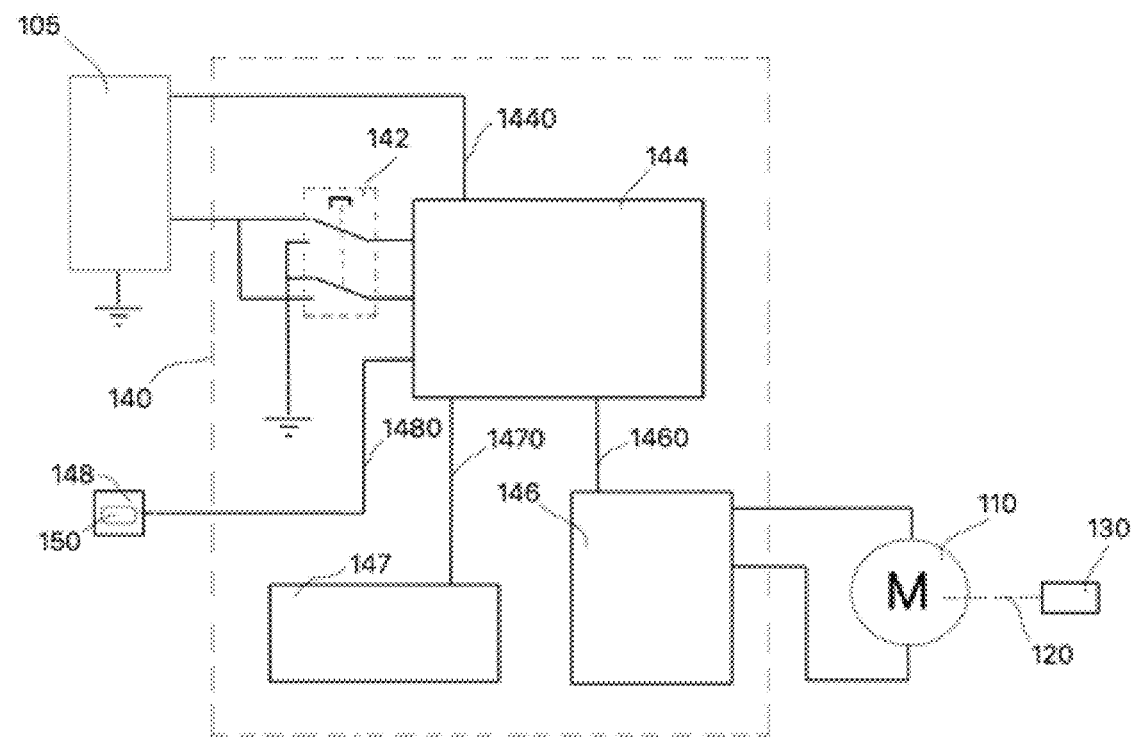

[Fig. 7]
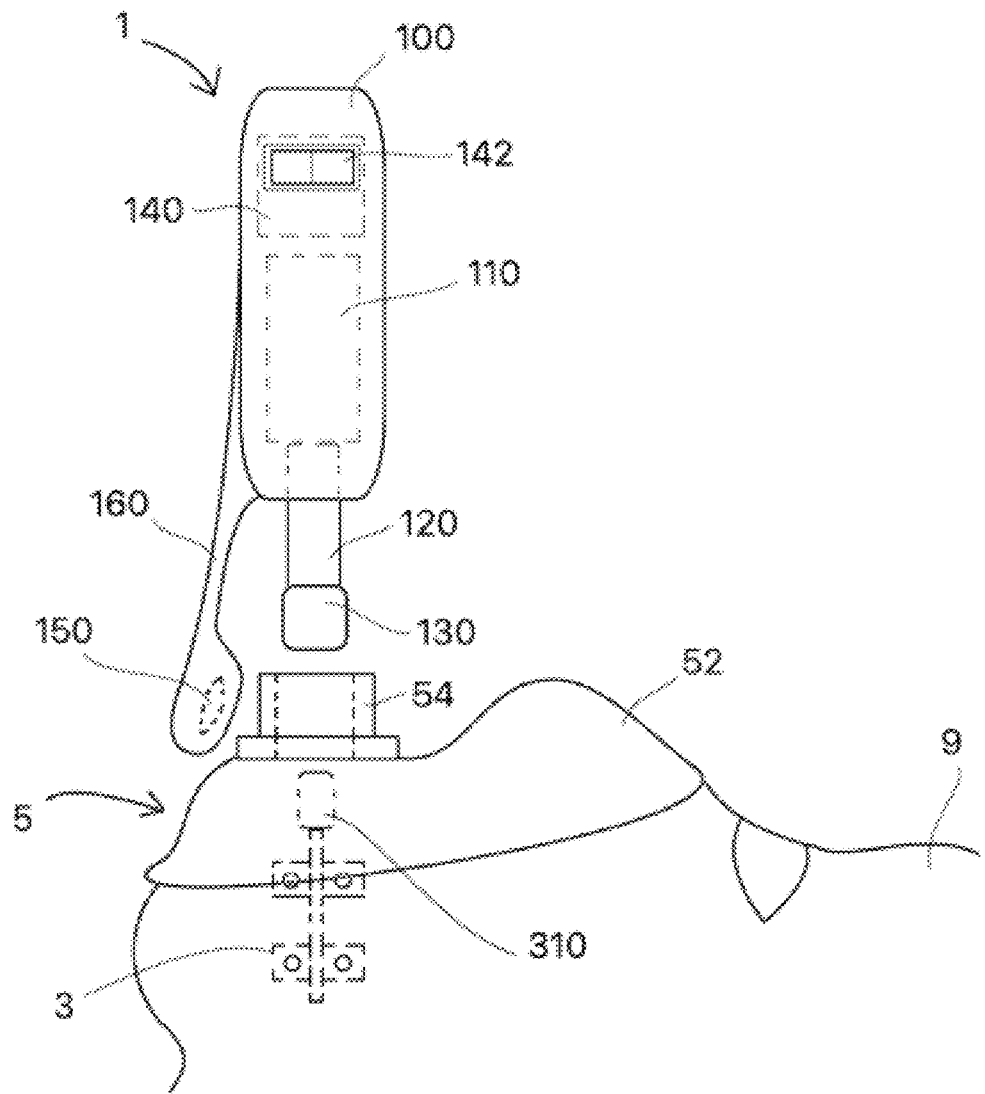
[Fig. 8]
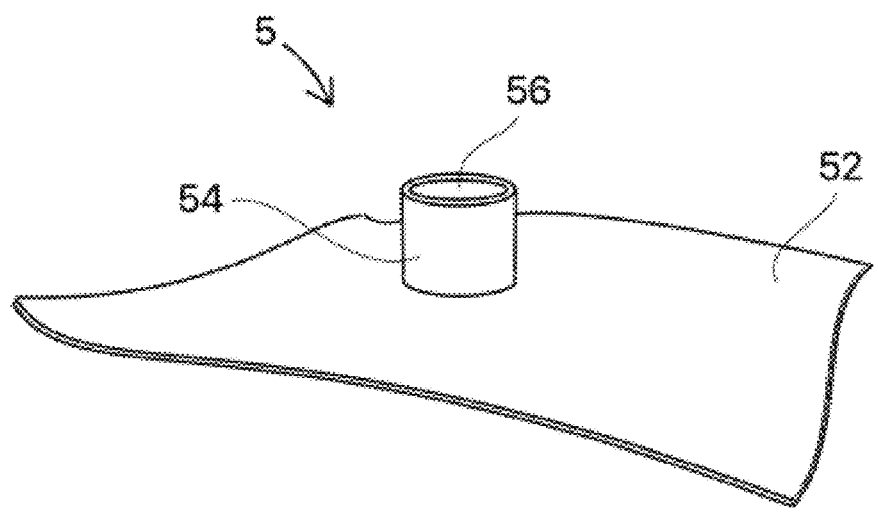

[Fig. 9]
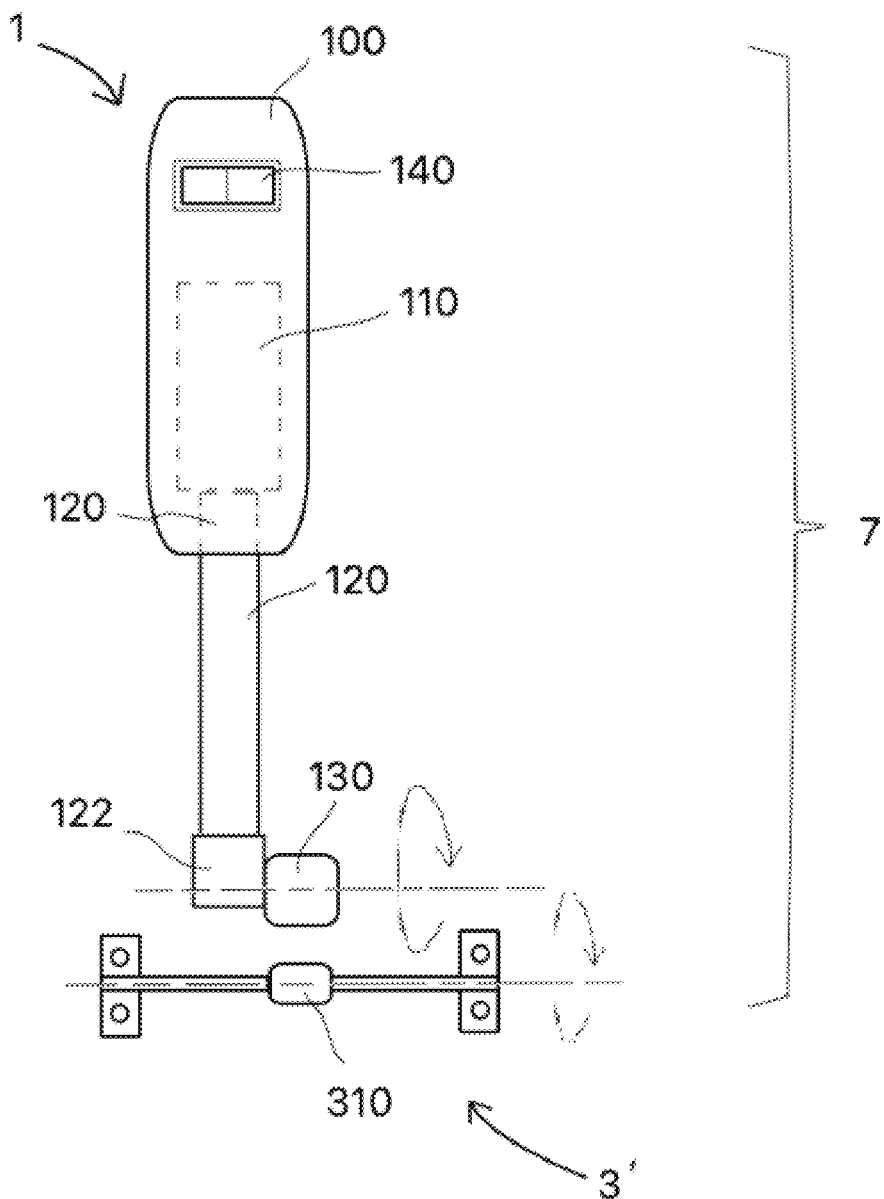

[Fig. 10]
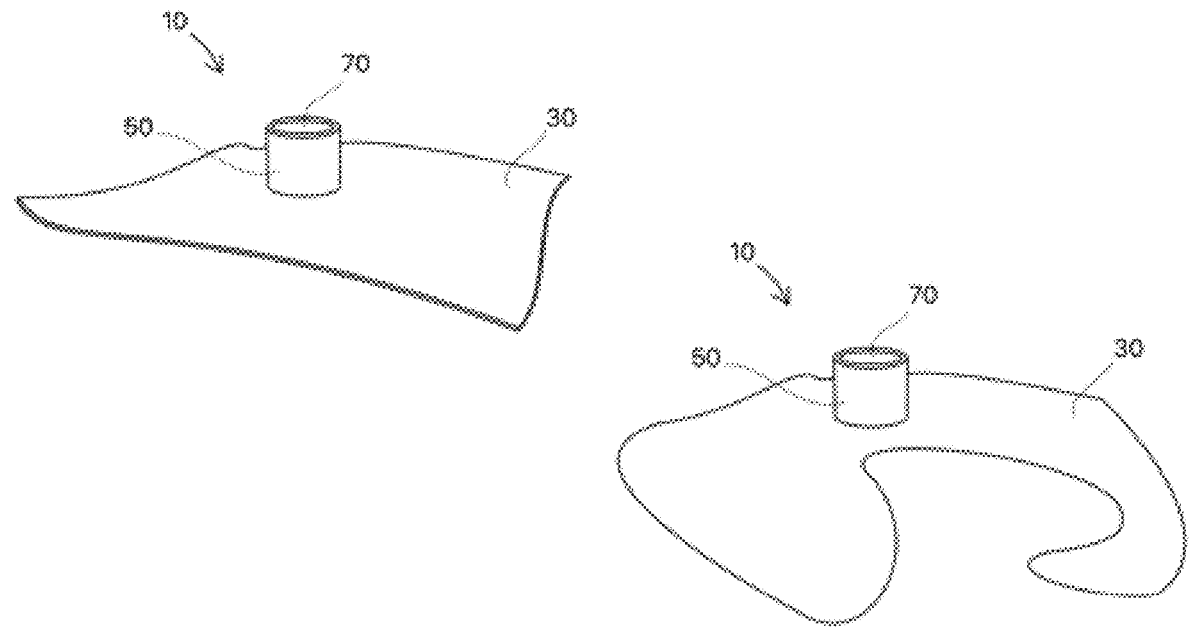
[Fig. 11]
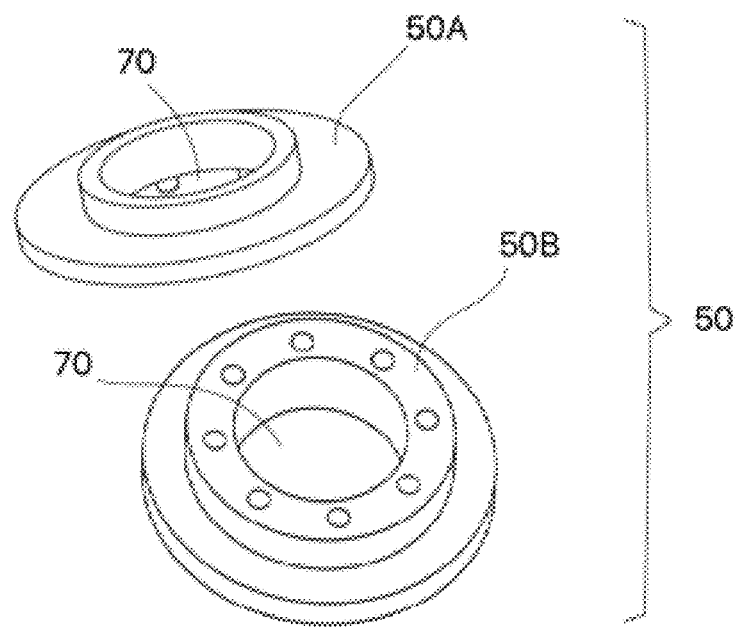

[Fig. 12]
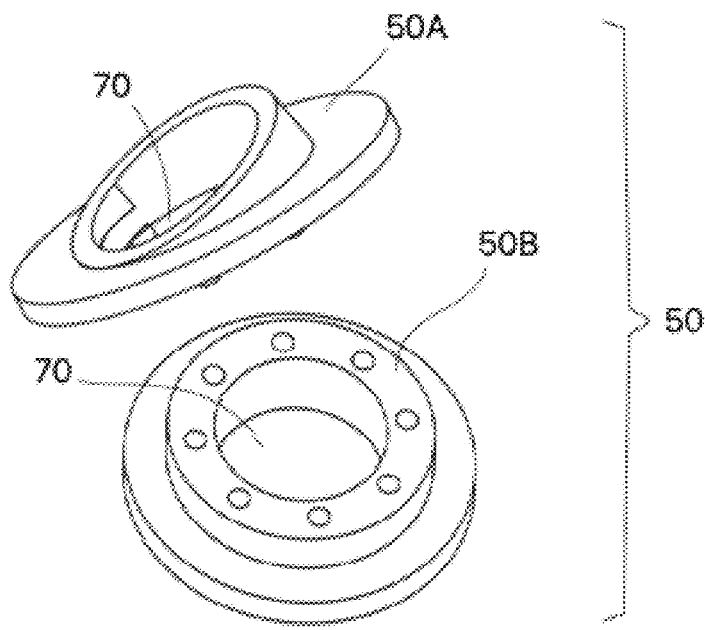
[Fig. 13]
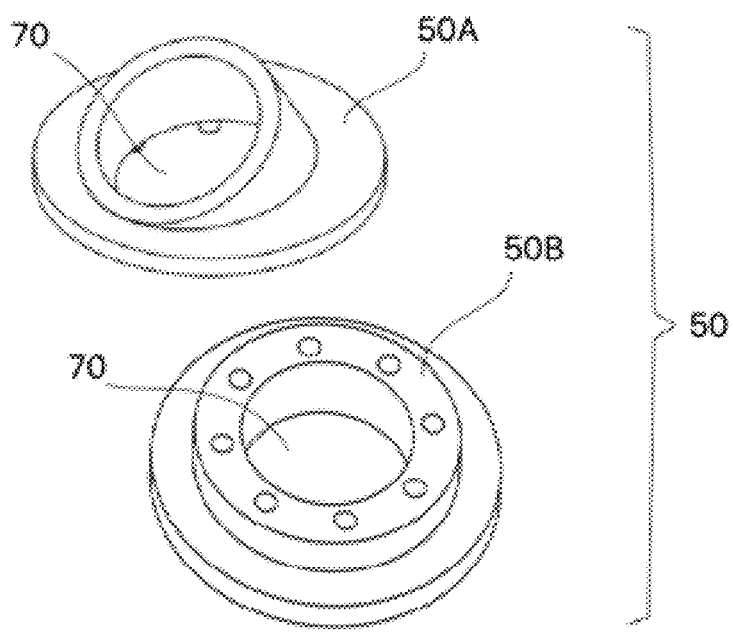

[Fig. 14]
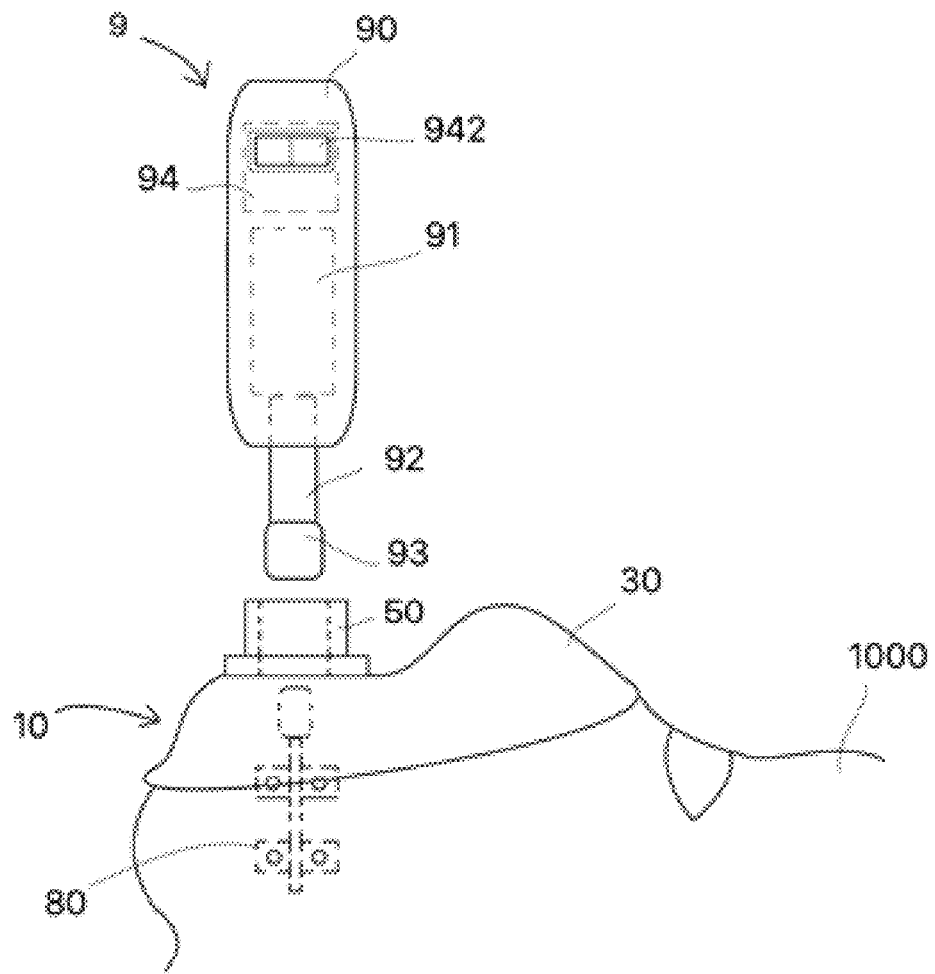
[Fig. 15]
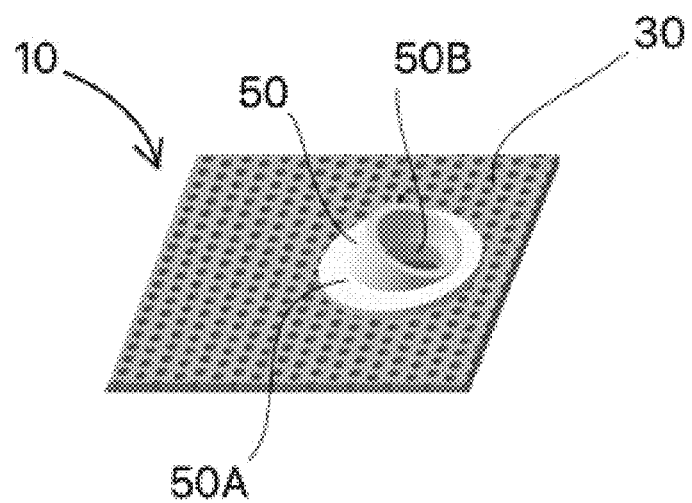

[Fig. 16]
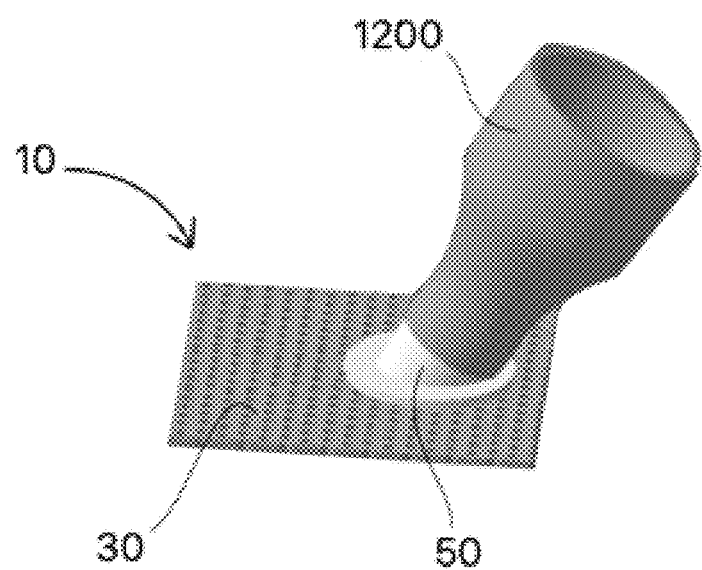

ACTIVATION TOOL FOR A BONE EXPANSION APPARATUS

The invention relates to the field of bone expansion apparatus such as, for example, a distraction plate apparatus or an expander. The invention relates more particularly to an activation tool for such apparatus as well as a device for helping to position the activation tool with respect to a bone expansion apparatus associated with it.

The state of the art, in particular in document WO 2017097998 A1, already describes a distraction plate apparatus designed to perform maxillofacial distraction. Such a distraction plate apparatus is attached to one side of a bone or to the side of adjacent bones of a subject and comprises a rotating magnet near one end of the distraction plate apparatus.

This magnet is rotated, using an external activation tool also bearing a magnet, positioned along a shaft corresponding to the rotation shaft of the magnet of the distraction plate apparatus, to perform bone distraction. To do this, the rotation of the magnet of the distraction plate apparatus causes the plates of the distraction plate apparatus to separate by means of a worm screw mechanism. The worm screw converts the rotational movement of the magnet of the distraction plate apparatus into a translational movement of one plate of the distraction plate apparatus relative to the other plate, causing the plates to separate.

The bone distraction assembly described in this document comprises an activation tool external to the subject bearing the distraction plate apparatus, the rotation of said tool causing the rotation of the magnet of the distraction plate apparatus by magnetic coupling.

This tool is nevertheless used manually and controlling the rotation of the magnet of the distraction plate apparatus requires considerable skill and vigilance by the operator.

The operator must therefore be correctly trained for this type of handling.

An error when handling the activation tool may result in bone destruction that is too small or, on the contrary, too large, or even close a surgical fracture that is useful for the treatment.

Documents EP 1272115 A1 and EP 3061614 A1 describe a surgical destruction device to apply a non-invasive tension or extension force on the skeleton of a patient or on an implant. The activation tool described in this document has a structure around a patient's limb. Document WO 2015168175 A1 describes a medical implant used to remotely adjust a dimension between two parts of a body, for example a distraction device, as well as a remote control to adjust a medical implant. Document US 2014128868 A1 describes a device and a method for repositioning bone structures.

The invention aims in particular to simplify the control of a bone expansion device such as, for example, a distraction plate apparatus or an expander whose elongation is controlled by the rotation of a magnet coupled to a worm screw.

Thus, the invention relates to an activation tool for a bone expansion apparatus, in particular for a distraction plate apparatus or an expander, for example for a distraction plate apparatus, the activation tool comprising a magnetic element solidly attached to a rotation shaft of the activation tool, the magnetic element being configured to interact, preferably coaxially, with a remote magnetic element borne by the bone expansion apparatus, the activation tool further comprising an electric motor configured to cause the rotation shaft to rotate, and a control module controlling the rotation of the rotation shaft.

In this case, the magnetic element of the activation tool and the remote magnetic element borne by the bone expansion apparatus simply have to be placed opposite each other. Thus, with such a coaxial configuration, rotation of the magnetic element of the activation tool about a rotation shaft of the magnetic element causes the remote magnetic element borne by the bone expansion apparatus to rotate about a rotation shaft of the remote magnetic element. In this coaxial configuration, the rotation shaft of the remote magnetic element coincides with the rotation shaft of the magnetic element of the activation tool. Thus, the rotation of the remote magnetic element borne by the bone expansion apparatus is obtained via the coaxial interaction between the magnetic element of the activation tool and the remote magnetic element borne by the bone expansion apparatus, without generating a tearing force on the bone expansion apparatus along a direction perpendicular to the rotation shaft of the remote magnetic element. This is particularly advantageous when the bone expansion apparatus is a distraction plate apparatus. Such a distraction plate apparatus is in fact often used on very young children and is, for example, attached to the bones using short screws, for example 5 mm long, or even plastic resorbable screws. The distraction plate apparatus is removed by tearing. Thus, the attachment of the distraction plate apparatus on the bones is relatively fragile and the adjustment of the distraction plate apparatus must not generate mechanical stresses likely to cause premature tearing. The intensity of the mechanical stresses likely to be exerted on the attachment of the plates to the bones must therefore remain as low as possible so that the distraction plate apparatus can be operated in complete safety.

According to other optional characteristics of the activation tool taken alone or in combination:

The activation tool is configured to control the direction of rotation of the rotation shaft. It is thus possible to move attachment elements of the bone expansion apparatus closer together or farther apart. In addition, if the required travel is exceeded, the separation obtained can be reduced, with the same accuracy.

The activation tool is configured to control the speed of rotation of the rotation shaft. It is thus possible to improve the precision and the control over the rotation of the rotation shaft and therefore over the separation or convergence of the mechanical elements of the bone expansion apparatus.

The activation tool control module comprises means for counting a number of portions of revolutions made during the rotation of the rotation shaft. Thus, the operator no longer has to count the revolutions or portions of revolutions of the rotation shaft of the activation tool, which considerably reduces the risk of error.

The activation tool control module comprises means for stopping the rotation of the rotation shaft when the rotation shaft has rotated by a predetermined number of revolutions, such that, as soon as the number of revolutions or portions of revolutions to be made has been reached, the rotation of the rotation shaft is interrupted, thus avoiding any risk of the operator exceeding the required number of revolutions by reacting too slowly.

The activation tool control module comprises means for programming a direction of rotation and a number of revolutions of the rotation shaft to be made in this direction of rotation.

Advantageously, the activation tool automatically controls the rotation of its rotation shaft, which once again considerably reduces the risk of error and simplifies the operation.

The activation tool comprises a magnetic field sensor, such as for example a Hall effect sensor, configured to measure a variation in the magnetic field emitted by the remote magnetic element borne by the bone expansion apparatus when the remote magnetic element is positioned in the extension of the rotation shaft of the activation tool on the side of the magnetic element solidly attached to the rotation shaft. Variations in a detected magnetic field can therefore be converted into information representative of the rotation of a remote magnetic element. The magnetic field sensor outputs a voltage whose variation is representative of the variation in the detected magnetic field.

The activation tool comprises a magnetic field measurement module configured to determine a rotation of the remote magnetic element of at least a predetermined number of revolutions about the separation axis of the bone expansion apparatus. Using this module, the rotation of a remote magnetic element can be determined from a variation in the voltage output by the magnetic field sensor. Advantageously, the rotation of the rotation shaft of the activation tool is then controlled according to the actual rotation of the remote magnetic element of the bone expansion apparatus, and not only according to the rotation of the magnetic element of the activation tool, by analysing the magnetic field variations measured. Thus, in case of incorrect magnetic coupling, and if sliding is observed between the rotation of the magnetic element of the tool and the rotation of the magnetic element of the expansion apparatus, the actual expansion made is nevertheless controlled.

The magnetic element of the activation tool comprises a magnet or a set of electromagnetic coils configured to generate a rotating magnetic field oriented perpendicular to the rotation shaft. For example, the magnetic element is a permanent magnet, preferably magnetised in a direction transverse to the rotation shaft of this permanent magnet of the activation tool. For example, the permanent magnet is cylindrical.

The remote magnetic element borne by the bone expansion apparatus is a permanent magnet, preferably magnetised in a direction transverse to the rotation shaft of this permanent magnet of the bone expansion apparatus. For example, the permanent magnet is cylindrical.

Thus, due to the magnetisation directions of the two permanent magnets, an attractive or repulsive force between these two magnets is reduced, compared with a configuration in which the magnets interact according to the direction of their magnetisation axes. The stresses generated by the distraction plate apparatus are thus reduced on the bone to which the distraction plate apparatus is attached, since these stresses could possibly tear off the distraction plate apparatus.

The magnetic element of the activation tool is configured to be driven by the electric motor, via the rotation shaft, at low rotational speed, for example at a maximum of between 12 and 30 revolutions per minute, preferably 18 revolutions per minute. Thus, there is no need to plan a reducer in the bone expansion apparatus, due to the low rotational speed of the remote magnetic element when it is coupled to the magnetic element of the activation tool.

The invention also relates to an assembly of a bone expansion apparatus, for example a distraction plate apparatus or an expander, and an activation tool according to the above-mentioned characteristics. The bone expansion apparatus is for example a distraction plate apparatus.

The supply of a bone expansion apparatus and of an associated activation tool, in the same assembly, optimises the characteristics of the magnetic elements so as to optimise the magnetic coupling.

Lastly, the invention relates to an assembly as described above, further comprising a device for helping to position the magnetic element of the activation tool with respect to the magnetic element borne by the bone expansion apparatus.

According to other characteristics of the assembly, the device for helping to position the magnetic element of the activation tool comprises a sheet of formable or thermoformable material configured to be attached to a subject and comprises a guide for positioning the magnetic element.

BRIEF DESCRIPTION OF THE FIGURES

The invention will be better understood on reading the following description, given solely by way of example and with reference to the accompanying drawings in which:

FIG. 1 is a schematic view of an activation tool for a bone expansion apparatus according to a particular and non-limiting embodiment of the invention, positioned opposite a distraction plate apparatus.

FIG. 2 is a simplified diagram of the activation tool of FIG. 1.

FIG. 3 is a schematic view of a first variant of the activation tool of FIG. 1.

FIG. 4 is a simplified diagram of the activation tool shown on FIG. 3.

FIG. 5 is a schematic view of a second variant of the activation tool of FIG. 1.

FIG. 6 is a simplified diagram of the activation tool shown on FIG. 5.

FIG. 7 is a schematic view of an activation tool for a bone expansion apparatus according to a particular and non-limiting embodiment of the invention, positioned opposite a distraction plate apparatus by means of the device for helping to position the tool with respect to a distraction plate apparatus borne by a subject.

FIG. 8 shows a device for helping to position the activation tool before shaping.

FIG. 9 shows a variant of the activation tool for a bone expansion apparatus already shown on FIG. 1, positioned opposite an expander.

FIG. 10 is a perspective view of a positioning helping device for helping to position equipment such as an activation tool according to a particular and non-limiting embodiment of the invention.

FIG. 11 is an exploded perspective view of an element for guiding the activation tool equipment shown on FIG. 10.

FIG. 12 is a view similar to FIG. 11, according to a first variant.

FIG. 13 is a view similar to FIG. 11, according to a second variant.

FIG. 14 illustrates a use of the positioning helping device shown on FIG. 10 according to the invention for the positioning of an activation tool for a distraction plate apparatus in the body of a subject.

FIG. 15 is a perspective view of a positioning helping device comprising the guiding element shown on FIG. 13.

FIG. 16 is a perspective view of the positioning helping device shown on FIG. 15, on which the end of a probe is positioned.

DETAILED DESCRIPTION

FIGS. 1 to 7 and 9 show an activation tool 1 for a bone expansion apparatus, in particular for a distraction plate apparatus 3 or an expander 3', respectively designed to elongate or separate bone parts. The distraction plate apparatus 3 is shown diagrammatically and is, for example, a distraction plate apparatus as described in document WO 2017097998, which describes a distraction plate apparatus, in particular a maxillofacial distraction plate apparatus, comprising for example: first and second attachment plates, a threaded rod, a tapped tube mounted on the threaded rod and attached to the second attachment plate, a socket receiving a part of the threaded rod free in rotation and fixed in translation—also referred to as a worm screw—and also the tapped tube fixed in rotation and free in translation, a permanent magnet contained in a hermetically sealed housing, extending along a main direction defining a main axis and magnetised along a direction transverse to the main direction, mounted in the distraction plate apparatus such that the rotation of the magnet about itself, about a rotation shaft parallel to the main axis, causes a relative rotation of the threaded rod with respect to the tapped tube, the permanent magnet being located at a distance from one of the ends of the distraction plate apparatus, measured along the direction of the rotation shaft of the magnet, less than or equal to 15 mm, preferably less than or equal to 10 mm, more preferably less than or equal to 5 mm, for example at one end in the extension of the worm screw.

FIG. 8 shows an accessory device 5 for helping to position the activation tool 1 with respect to the distraction plate apparatus 3.

FIG. 1 shows an activation tool 1 according to an embodiment of the invention. The activation tool 1 comprises a main body 100 containing an energy source 105 (not shown on FIG. 1) and an electric motor 110 designed to be powered by the energy source 105.

The energy source 105 is preferably a battery rechargeable using an induction wireless charging interface. The electric motor 110 is a direct current motor comprising two connection terminals, a stator, a rotor and a central rotation shaft. The rotor of the electric motor 110 is configured to perform an angular rotation about the rotation shaft of the motor 110. The direction of rotation of the rotor of the motor 110 depends on the polarity of the voltage applied across the connection terminals of the motor 110. The electric motor 110 is coupled to the rotation shaft 120. The coupling optionally comprises a mechanical assembly such as a reducer, so that a rotation of one revolution of the rotor of the electric motor 110 only causes the rotation shaft 120 to rotate through a portion of a revolution. The use of a reducer is all the more advantageous if the nominal speed of rotation of the motor is high.

According to a preferred embodiment of the invention, the rotation shaft 120 is driven by the electric motor 110 at low speed of rotation, for example at a speed of between 12 and 30 revolutions per minute, preferably at a speed of 18 revolutions per minute, for each of the two directions of rotation. The rotation shaft 120 extends outside the body 100 of the activation tool 1. The rotation shaft 120 bears a magnetic element 130 positioned at its end located outside the body 100. Thus, the magnetic element 130 is configured to be driven by the motor 110, via the rotation shaft 120, at low speed of rotation, for example at a maximum of between 12 and 30 revolutions per minute, preferably 18 revolutions per minute. Consequently, there is no need for a reducer in the distraction plate apparatus 3 between the remote magnetic element 310 and the worm screw, thereby limiting the size of the distraction plate apparatus 3. The magnetic element 130 is for example a permanent magnet, even a neodymium type magnet.

Advantageously, the use of a reducer allows the rotation of the rotation shaft 120 and therefore the rotation of the magnetic element 130 to be controlled more precisely. The term "rotation shaft" must be interpreted in this case as being a mechanical assembly configured to transmit the angular rotation of the rotor of the motor 110 to the magnetic element 130. The magnetic element 130 is solidly attached to the rotation shaft 120. The magnetic element 130 can be interchangeable or not, depending on how it is attached to the rotation shaft 120.

Advantageously, when the magnetic element 130 is interchangeable, it can be adapted to a plurality of types of bone expansion apparatus.

The magnetic element 130 is magnetised such that the resulting magnetic field is oriented perpendicular or substantially perpendicular to the rotation shaft 120.

The magnetic element 130 is a neodymium type magnet. Those skilled in the art will know how to choose a neodymium magnet according to the criteria of distance between the magnetic element 130 of the activation tool 1 and the remote magnetic element 310 as well as the torque to be transmitted on the mechanical expansion link of the expansion apparatus to be controlled.

The activation tool 1 also comprises a 3-position switch 140. A first position of the 3-position switch 140 corresponds to a configuration in which the motor 110 rotates in a first direction of rotation (called clockwise). A second position of the switch 140 corresponds to a configuration in which the motor 110 rotates in a second direction of rotation (called anti-clockwise) opposite to the first direction of rotation. Lastly, a third position of the switch 140 corresponds to no rotation of the motor.

The activation tool 1 shown on FIG. 1 is positioned opposite a distraction plate apparatus 3 bearing a magnetic element 310 remote from the magnetic element 130 of the activation tool 1. The distraction plate apparatus 3 is borne by a subject requiring a bone expansion such as a bone distraction. The distraction plate apparatus 3 is arranged in the body of the subject.

The magnetic element 310 of the distraction plate apparatus is mounted at the end of a hinged rod adapted to control the separation of two plates. Mounting the magnetic element 310 at the end of the worm screw of the distraction plate apparatus 3 allows magnetic coupling between a magnetic element outside the body of the subject and the magnetic element 310 inside the body of the subject. The two plates of the distraction plate apparatus 3 are configured to be attached to a bone or to neighbouring bones of the subject requiring bone elongation. Such mechanisms used to control the separation of plates by means of a worm screw are known. It is also known to arrange a magnetic element at the end of a worm screw of a distraction plate apparatus so as to be able to rotate the worm screw using a magnetic element outside the body of a subject bearing a distraction plate apparatus.

The magnetic element 310 of the distraction plate apparatus 3 is magnetised such that the resulting magnetic field is perpendicular or substantially perpendicular to the rotation shaft bearing it. Thus, magnetic coupling to rotate the magnetic element 310 can be achieved by means of an exterior magnetic element (such as the magnetic element 130), positioned near the magnetic element 310, and magnetised such that the resulting magnetic field is perpendicular of substantially perpendicular to the rotation shaft bearing it.

To perform a bone expansion movement, a user of the activation tool 1 positions said tool such that the magnetic element 130 of the activation tool is positioned opposite the magnetic element 310 of the distraction plate apparatus. The term "opposite" must be interpreted in this case as meaning that the rotating magnetic elements 130 and 310 are positioned such that their rotation shafts substantially coincide and are for example coaxial, to produce magnetic coupling capable of transmitting the angular rotational movement of the magnetic element 130 to the remote magnetic element 310 of the distraction plate apparatus.

After positioning the activation tool, the user positions the switch 140 in order to select the direction of rotation corresponding to a bone expansion movement, when the magnetic element 310 is rotated under the effect of the magnetic coupling with the magnetic element 130 of the activation tool 1.

When the switch 140 is positioned so as to select the direction of rotation corresponding to a bone expansion movement, the rechargeable battery 105 outputs a suitable voltage across the terminals of the motor 101. The rotor of the motor 101 then makes a rotation transmitted to the rotation shaft 120 which is attached to it, and to the magnetic element 130. The rotation of the magnetic element 130 rotates the remote magnetic element 310 of the distraction plate apparatus, positioned in the body of the subject, by magnetic coupling.

The internal mechanism of the distraction plate apparatus then performs a bone expansion such as a distraction.

The clockwise rotation of the rotation shaft 120 of the activation tool 1 causes for example the plates of the distraction plate apparatus 3 to separate during magnetic coupling between the tool and the distraction plate apparatus. In contrast, the anti-clockwise rotation of the shaft 120 causes the plates of the distraction plate apparatus 3 to converge.

Advantageously, the use of an electric motor of low rotation frequency (speed), or the use of a reducer coupling the rotation shaft of the rotor of the motor 110 to the rotation shaft 120 improves the control over the rotation of the remote magnetic element 310.

Advantageously, the part of the rotation shaft 120 outside the body 100 of the activation tool 1 bears one or more visual indicators allowing the number of rotations of the rotation shaft 120, and therefore of the magnetic element 130, to be counted quickly and easily.

These visual indicators can be marks, coloured sections or any other visual element likely to indicate to the user that a full revolution or a portion of a revolution of the rotation shaft 120 has been completed.

According to a preferred embodiment, the rotation shaft 120 is cylindrical. According to variants, the rotation shaft may have a square, pentagonal, hexagonal or octagonal shape or a predetermined number of lateral flats with at least one portion bearing visual indicators adapted to easily indicate a rotation of a predetermined number of portions of a revolution.

If a movement is made causing an excessive separation of the plates of the distraction plate apparatus, the user can use the 3-position switch 140 in order to select a rotation opposite to that causing the separation, thus making a correction.

When a rotation of the rotation shaft 120, and therefore of the magnetic element 130 has been made as required, the user sets the 3-position switch to the position corresponding to no rotation of the motor.

According to this embodiment, the 3-position switch acts like a control module controlling the rotation of the rotation shaft 120.

FIG. 2 is a block diagram of the activation tool 1. The switch 140 operating like a control module controlling the rotation of the rotation shaft 120 is connected between the voltage source 105 and the electric motor 120.

The contacts of the switch 140 are positioned so that a nominal voltage, or a reverse voltage, of the voltage source 105 can be applied across the terminals of the direct current electric motor 110, which in this case corresponds respectively to a rotation of the motor rotor in a first direction of rotation or a rotation of the motor rotor in a second direction of rotation, opposite to the first direction of rotation.

An intermediate position isolates the electric motor 110 from the voltage source 105, which in this case means that no voltage is supplied to the motor and consequently that its rotor and therefore the rotation element 120 do not rotate. The electric motor 110 is mechanically coupled to the magnetic element 130 via the rotation shaft 120.

FIG. 3 shows the activation tool according to a second embodiment of the invention. According to this second embodiment of the invention, the control module 140 controlling the rotation of the rotation shaft 120 comprises an embedded control unit configured to control the electric motor 110 via a power interface circuit depending on the position of a 3-position switch 142.

According to this embodiment of the invention, the embedded control unit of the control module 140 controlling the rotation of the shaft comprises at least one microcontroller adapted to control the electric motor 110 using control signals supplied by the 3-position switch 142 and control signals representative of the position and/or of the rotation of the rotation shaft 120. The control signals representative of the position and/or of the rotation of the shaft 120 are generated using means for detecting the rotation and the position of the shaft 120, for example optoelectronic means, and applied at the input of the control unit.

For example, the rotation shaft 120 may bear lateral fins arranged to sequentially interrupt a light or infrared signal emitted and received by optoelectronic means coupled to the embedded microcontroller of the control unit.

The lateral fins used to detect the rotation of the rotation shaft 120 may consist of a wheel, mounted centred on the rotation shaft 120 and comprising openings regularly spaced around the periphery of the wheel. This type of means for detecting an angular rotation is well known and is used to slave the rotational control of an element, such as the rotation shaft 120, depending on the movement actually detected. Advantageously, the ability to precisely detect the position of the rotation shaft 120 and therefore its rotation can be used to control the speed of rotation via the control unit.

FIG. 4 is a block diagram of the activation tool according to the second embodiment. The 3-position switch 142 is connected to input ports of the microcontroller of the control unit 144. The power interface circuit 146 is used to control the rotation of the electric motor 110 using output ports of the microcontroller of the control unit 144.

The power interface 146 comprises in particular amplification and protection circuits to supply the currents required to rotate the motor 110, using elementary output ports, such as logic gate type outputs or open collector outputs of the control unit.

Obviously, the control unit 144 comprises all the elements traditionally used to implement an embedded controller, such as, given as non-limiting examples, a reset circuit, one or more clock circuits, a random access memory module used to execute embedded software routines, a read-only memory module used to store executable code instructions to execute software routines, standby circuits (low energy consumption mode), a battery charge power supply supervision and/or control circuit 105, one or more analogue-digital and digital-analogue converters, input ports and output ports, interrupt inputs, electrostatic discharge protection circuits. These elements are not described in further detail since they are not required to understand the invention.

Advantageously, the embedded software stored in a portion of read-only memory can be updated using a communication interface provided for this purpose. The communication interface may be wired or wireless. An updated version of all or part of the embedded software can be downloaded by coupling with a remote terminal such as, for example, a computer, a tablet or a smartphone, connected to the internet or provided with the software and hardware elements required for the update.

According to an embodiment of the invention, the control unit 144 is programmed to generate control signals for controlling the rotation of the electric motor 110 depending on the position of the 3-position switch 142 and the actual rotation of the rotation shaft 120.

Thus, if a user sets the 3-position switch 142 to the position defined to rotate the rotation shaft 120 in the direction required to separate the plates of the distraction plate apparatus 3 when the tool 1 is magnetically coupled to the distraction plate apparatus 3, the control unit 144 will control the power circuit 146 to control the rotation of the motor in the required direction until the detection and position means have detected an angular rotation corresponding to a predetermined number of revolutions or portions of revolution of the rotation shaft 120.

When the shaft 120 has been driven by the electric motor 110 through a predetermined angle of rotation, the control unit programmed to measure the angle of rotation using signals from optoelectronic means inhibits the control signals for controlling the rotation of the motor 110 such that the rotation stops.

According to a variant of the embodiment, the motor is a stepper motor and the microcontroller of the control unit 144 is configured to generate signals adapted to control a stepper motor via the power interface circuit 146. Advantageously, such a variant removes the need for means to measure the position and/or the angular rotation of the rotation shaft 120 since the rotation of a stepper motor is defined by a series of elementary rotational movements each corresponding to a step and therefore to a predefined angle of rotation about the rotation shaft.

According to a variant of the embodiment, the control unit is programmed to detect a number of (activation) pulses on the switch 142, during a predetermined period, corresponding to the definition of the number of revolutions or portions of revolution to be made in one of the two directions of rotation, to then cause the rotation of a number of portions of revolution corresponding to the number of pulses detected during the period.

Thus, if for example a user successively activates the switch 142 ten times to generate an input signal on the control unit 144 to cause a rotation of the shaft 120 resulting in bone expansion during magnetic coupling between the activation tool 1 and the distraction plate apparatus 3, over a predetermined period of 5 seconds, for example, the control unit will control the motor 110 in order to rotate the shaft 120 by ten elementary angular steps. An elementary angular step can be, for example, a quarter turn, in other words a 90-degree rotation of the rotation shaft 120.

According to a variant of the embodiment, the control module 140 further comprises a user interface adapted to enter a number of revolutions or portions of revolution to be made, as well as information representative of the required direction of rotation.

FIG. 5 shows an activation tool 1 for a bone expansion apparatus according to a third embodiment of the invention. The activation tool 1 comprises, according to this third embodiment, an arm 160 bearing an inductive sensor 150 adapted to measure magnetic field variations (a magnetic field sensor). The arm 160 of the activation tool 1, extending from the body 100 of the activation tool 1, is configured to be positioned near the magnetic element 310 inside the subject bearing a bone expansion apparatus, during magnetic coupling between the magnetic element 130 and a remote magnetic element 310 of a bone expansion apparatus attached in the body of a subject.

The inductive sensor 150 is configured to detect magnetic field variations by using the Hall effect. The inductive sensor 150 converts the magnetic field variations into voltage variations.

The voltage variations thus obtained are measured by the control unit 144. The control unit therefore comprises an analogue-digital converter.

The inductive sensor 150 thus forms a magnetic field sensor configured to measure a variation in the magnetic field emitted by the remote magnetic element 310 borne by the bone expansion apparatus 3 when the remote magnetic element 310 is positioned in the extension of the shaft 120 of the activation tool on the side of the magnetic element 130 solidly attached to the shaft 120.

Advantageously, use of the magnetic field sensor 150 allows precise measurement of a number of revolutions or portions of revolution actually made by the magnetic element 310 inside the subject bearing the distraction plate apparatus 3, and therefore better control over the bone expansion.

FIG. 6 is a block diagram of the activation tool 1 according to a third embodiment of the invention for which the activation tool 1 comprises an inductive sensor 150 assembled on a support 148 near the end of the arm 160 extending the body 100 of the activation tool 1.

According to this third embodiment, the activation tool 1 comprises, in addition to the control unit 144 supplied by the power supply connection 1440, the power interface circuit 146, connected to the control unit via a connection interface 1460 and the switch 142, a user interface module 147 connected via a connection interface 1470.

Advantageously, the user interface module 147 comprises a display module adapted to display information such as a number of revolutions or portions of revolution to be made and a direction of rotation, as well as information representative of the number of revolutions or portions of revolution to be made and/or made.

The display module comprises, as non-limiting examples, a Liquid Crystal Display (LCD) or a Light Emitting Device (LED).

Advantageously, the number of revolutions or portions of revolution to be made can be entered (programmed) by the user of the activation tool via an input interface connected to the control unit 144.

The number of revolutions or portions of revolution can be entered using a set of keys or keys corresponding to predefined functions or used to move through the drop-down menus displayed on the display module. All these functions are performed under the control of the control unit 144, by executing embedded software routines provided for this purpose and executed by the microcontroller of the control unit 144.

Thus, a user of the activation tool 1 can program it to perform a predefined number of revolutions or portions of revolution in a given direction of rotation. For example, a user can program the activation tool 1 to control a clockwise rotation corresponding to 3.75 revolutions.

According to a variant, the user can increment the number of revolutions or portions of revolution to be made by successive presses on a dedicated key and a long press to reset the preprogrammed number of revolutions or portions of revolution.

Similarly, the direction of rotation can be defined, for example, by successive rapid presses, to make a distinction between controlling the direction of rotation and defining the number of revolutions or portions of revolution to be made.

Obviously, other ways of encoding the information to be entered can be used, the user's objective being to be able to program a direction of rotation and a number of portions of revolution to be made using the activation tool 1.

The control module 140 comprising the control unit 144 and its peripherals 142, 146, 147, according to the invention, therefore provide better control over the operation of a bone expansion apparatus such as the distraction plate apparatus 3, and therefore simplify the bone expansion controls of distraction plate apparatus or of expanders while guaranteeing better precision.

Advantageously, the control means (entry, encoding or programming) for controlling a number of revolutions or portions of revolution to be made in a given direction of rotation and the display means of the activation tool 1 may be combined in the same module or element, in the form of a touch screen, for example.

Thus, using the activation tool 1 according to the invention, a user not specifically trained for this type of operation can control a bone expansion, considerably reducing the risk of making an insufficient bone expansion or an excessive bone expansion.

Advantageously, the bone expansion can therefore be controlled by a non-specialist user or a user with no specific training.

The more effective the magnetic coupling between the magnetic elements 130 of the activation tool 310 and of the distraction plate apparatus 3, the greater the efficiency and precision of the activation tool.

To optimise the magnetic coupling between these elements, the magnetic elements 130 et 310 can be replaced by support elements, bearing a plurality of magnetic elements, each magnetised in order to optimise the magnetic coupling between the two support elements. The support elements then appear for example like cylindrical heads each comprising cylindrical magnets uniformly distributed around a longitudinal shaft. Thus, for example, the magnetic element 130 of the activation tool 1 can be replaced by a cylindrical head support comprising 3 separate magnetic elements and the magnetic element 310 of the distraction plate apparatus 3 can be replaced by a cylindrical head support bearing 3 other separate magnetic elements magnetised so as to complement those of the activation tool 1, in order to increase the magnetic coupling between the activation tool 1 and the distraction plate apparatus 3. The coaxial interaction between the magnetic element 130 and the magnetic element 310 is then achieved coaxially with respect to the longitudinal shaft.

According to a variant of the embodiments described, and if the magnetic coupling between the elements 130 and 310 is defined optimally when the magnetic elements 130 and 310 are positioned coaxially, in other words when the rotation shaft of the magnetic element 130 and the rotation shaft of the magnetic element 310 coincide, the activation tool 1 can be judiciously positioned opposite the distraction plate apparatus 3 using the device 5 for helping to position the activation tool 1.

FIG. 7 shows a position of the activation tool 1 opposite the distraction plate apparatus 3 borne by a subject 9. The distraction plate apparatus is attached in the body of the subject 9, on the lower jaw, on the left side of the mouth. The magnetic element 310 is arranged in the body of the subject, not far from the mouth.

Advantageously, the device 5 for helping to position the activation tool 1 comprises a plate of thermoformable material 52 and a hollow end-piece 54. The shape of the cavity of the end-piece 54 is complementary to the shape of the magnetic element 130 of the tool 1.

The positioning helping device 5 has been modelled by thermoforming to adapt to the physiology of the subject 9 when fitting the distraction plate apparatus 3 during surgery.

During the installation, the practitioner modelled the plate 52 of thermoformable material to define a surface profile complementary to that of the face of the subject 9. Such a plate is modelled after simply increasing the temperature with hot water. The end-piece 54 was then assembled by crimping, clipping or bonding on an opening of the plate made at the location corresponding to the position of the magnetic element 310 arranged in the body of the subject 9 and invisible from the outside after the surgery.

The end-piece 54 can be assembled on the plate 52 of thermoformable material before or after modelling the plate.

Thus, the positioning helping device 5 modelled on the face of the subject 9, can be repositioned quickly and easily on the face of the subject 9 after it has been shaped, and therefore define a guide for positioning the magnetic element 130, so that it can be placed quickly and easily in the alignment of the magnetic element 310 inside the subject 9.

When the positioning helping device 5 is positioned on the face of the subject 9, the cavity of the end-piece 54 can receive the magnetic element 130, thus arranged opposite the magnetic element 310.

Advantageously, this configuration makes it possible to place the inductive sensor 150 near the magnetic element 310 inside the subject and to measure the actual rotation of said element by detecting the variation in the magnetic field received by the inductive sensor 150.

According to an embodiment of the invention, the cavity of the end-piece 54 comprises a stop to prevent the magnetic element 130 from touching the skin of the subject 9 during the rotation of the magnetic element 130. Advantageously, this avoids discomfort for the subject 9.

According to an embodiment of the invention, the end-piece 54 may have a cavity substantially perpendicular to the contact surface between the plate 52 and the face of the subject 9 at the place where the end-piece 54 is positioned. According to variants, the end-piece 54 has a cavity whose longitudinal axis is oriented obliquely with respect to the perpendicular at the contact surface between the plate 52 and the face of the subject 9.

Advantageously, this allows the magnetic element 130 to be positioned coaxially with respect to the magnetic element 310, depending on the position of the distraction plate apparatus 3 in the body of the subject 9.

FIG. 8 shows the device 5 for helping to position the activation tool 1, before shaping the plate of thermoformable material 52 on a subject. The plate of thermoformable material 52 bears an end-piece 54 having a cylindrical opening 56 configured to receive the magnetic element 130 of the activation tool 1.

FIG. 9 shows a variant of the activation tool according to a non-limiting embodiment for which the rotation shaft 120 comprises an angular part 122 with internal gears to drive the magnetic element 130 about a shaft perpendicular to the rotation shaft of the motor 110. The angular part 122 typically comprises an angle gearbox comprising two bevel gears.

FIG. 9 shows the activation tool 1 positioned opposite an expansion apparatus 3' of expander type, designed to separate bone parts of a subject. For example, the apparatus 3' can be solidly attached to right and left side parts of the upper gum of a subject, to progressively enlarge the palate. The expander 3' can be configured to be attached to bone parts, on rings solidly attached to the teeth of a subject, or to dental braces (case of maxillary or symphyseal distraction), for example.

The magnetic element 310 of the expander is solidly attached to a shaft such as a threaded rod comprising worm screw connections with attachment elements located at the ends of the rods. The two threads have opposite pitches.

The threads each side of the magnetic element 310 are such that when the magnetic element 310 rotates in one direction, the attachment elements move apart to separate the parts connected thereto. Inversely, when the magnetic element 310 rotates in the opposite direction, the attachment elements converge.

In other words, the activation tool 1 controls the bone expansion performed by a bone expansion apparatus, such as a distraction plate apparatus 3 or the expander 3'. The activation tool 1 comprises the magnetic element 130 solidly attached to the rotation shaft 120 of the activation tool 1. The magnetic element 130 is configured to interact with the remote magnetic element 310 borne by the bone expansion apparatus 3. The activation tool 1 further comprises the electric motor 110 configured to rotate the shaft 120, and the control module 140 controlling the rotation of the shaft 120.

The activation tool 1 is configured to control the direction of rotation of the shaft 120.

The control module 140 is configured to control the speed of rotation of the shaft 120.

The activation tool comprises means for counting a number of revolutions or portions of revolution made during the rotation of the shaft 120.

The control module 140 of the activation tool 1 comprises means for stopping the rotation of the shaft when the shaft has rotated through a predetermined number of revolutions.

The control module 140 comprises, via the microcontroller inside the control unit 144, means for programming a direction of rotation and a number of revolutions of the shaft to be made in this direction of rotation.

The activation tool 1 comprises the magnetic field inductive sensor 150 configured to measure a variation in the magnetic field emitted by the remote magnetic element 310 borne by the bone expansion apparatus 3 when the remote magnetic element 310 is positioned in the extension of the shaft 120 of the activation tool 1, on the side of the magnetic element 130 solidly attached to the shaft 120.

The activation tool 1 comprises a magnetic field measurement module configured to determine a rotation of the remote magnetic element 310 of at least a predetermined number of revolutions or portions of revolution about the separation axis of the bone expansion apparatus 3. The measurement module is for example the magnetic field sensor 150.

The bone expansion apparatus 3 and the activation tool 1 form an assembly 7 required to perform a bone expansion operation offering greater precision and simplifying the execution of successive bone expansion operations by a user with no specific training.

The assembly 7 required to perform bone expansion operations may advantageously be completed by the device 5 for helping to position the magnetic element of the tool 1, and therefore of the magnetic element 130 with respect to the magnetic element 310 borne by the bone expansion apparatus 3.

The assembly 7 then comprises the device 5 for helping to position the magnetic element 130 of the tool 1, said device comprising a sheet of thermoformable material 52 which can be attached to and shaped on the subject 9 and which comprises the guide 54 for positioning the magnetic element 130.

In addition, according to variants, the rotation shaft 120 can be replaced by a non-rectilinear rotating system comprising intermediate mechanical elements, such as gears or universal joints configured to transmit the angular rotation of the motor 110 to the magnetic element 130. Thus, the magnetic element 130 can be rotated about an axis different from the main axis of the body 100 of the activation tool 1 and adapt to distraction plate apparatus or expanders of different shapes.

According to these variants, it is advantageously possible to adapt to different configurations of bone expansion apparatus and in particular to different configurations for positioning the rotation shaft of the remote magnetic element 310.

According to another variant, the non-rectilinear rotating system used to transmit the angular rotation of the motor 110 to the magnetic element 130 comprises a flexible cable inside a sheath, the sheath itself being inside a semi-rigid tube whose shape can be modified manually to adapt to different types of bone expansion apparatus.

According to another variant, the activation tool 1 comprises a wireless communication interface adapted to two-way short-range communications. The wireless interface may be of type compatible with the wireless communication standard usually called Bluetooth® or any one of its upgrades.

According to another variant, the wireless communication interface may be of type WiFi®, or any one of its upgrades.

Advantageously, a wireless communication interface allows the use of a remote control unit such as, for example, the control unit of a smartphone device, under the control of a dedicated software application.

Advantageously, such an interface can be used to transfer, to a remote third party, information useful for the treatment of a subject such as, for example, data representative of the measurements taken by the magnetic sensor 150 of the activation tool 1. This third party may be for example a relative of a subject undergoing the distraction, or a practitioner such as their doctor, who would then be in a position to remotely control correct execution of the bone distraction operations.

A remote control unit allows the use of relatively simple embedded software in the activation tool 1, and simplifies upgrades or updates of the control means, in this case mainly implemented on the smartphone.

Another advantage is that the equipment can be configured remotely, for example by a practitioner.

In addition, using a smartphone simplifies the architecture of the embedded systems of the activation tool 1.

According to a variant, the energy source 105 is a removable, non-rechargeable battery. According to another variant, the energy source 105 is a switched-mode power supply module designed to be connected to the "mains" electricity network via a wall socket.

According to a variant, the shaft 120 is a fixed shaft and the activation tool does not comprise a motor. According to this variant, the magnetic element 130 consists of a plurality of electromagnetic coils arranged to form a circular or substantially circular magnetic element, around the shaft 120, said coils having a power supply controlled by the control module 140 and being configured to allow the generation of a rotating magnetic field oriented perpendicular to the shaft 120. Such an architecture can therefore generate a magnetic field similar to that created when the magnetic element 130 is a magnet.

The invention is not limited to the embodiments described above and other characteristics described in each of the above-mentioned embodiments may be combined.

The invention also relates to a device for helping to position equipment with respect to the body of a subject and more particularly with respect to a visible or non-visible target object located in the body of a subject.

Such equipment is for example the activation tool 1 described above.

The invention also relates to the field of devices for helping to position equipment, for example in the medical, paramedical or industrial field. The invention relates more particularly to a device for helping to position equipment with respect to a support in an object or in the body of a person.

The state of the art, in particular in patent application WO 2017097998, already describes a distraction plate apparatus implanted in the body of a subject and designed to perform maxillofacial distraction.

Such a distraction plate apparatus comprises two plates attached to one side of a previously fractured bone or to the side of adjacent bones of a subject and comprises a magnet that can be rotated near one end of the distraction plate apparatus.

The distraction plate apparatus may also be used with teeth or bands of dental braces.

In such a distraction plate apparatus, the magnet is cylindrical and magnetised in a direction perpendicular to its longitudinal axis. The magnet is also solidly attached to a worm screw whose rotation causes a tapped tube to translate, thereby increasing the distance between two plates.

The magnet is therefore positioned inside the body, and the distraction plate apparatus can be actuated from the outside by magnetic or non-magnetic (mechanical) coupling.

The elongation of the distraction plate apparatus can therefore be controlled from outside the patient, without any contact and without the need for an activation tool passing through the patient's skin or mucous membrane. With this system, there is no need to implement a hinged rod passing through the patient's tissues.

A magnetised magnet, for example cylindrical, is simply positioned opposite the internal magnet so that the rotation of the external magnet about its axis causes the rotation of the internal magnet.

In case of magnetic coupling, the coupling is efficient if the magnets are correctly positioned with respect to each other and if their respective shafts coincide or are as close as possible to each other.

A disadvantage of the system is that it is difficult to position external equipment (for example an activation tool) with respect to an element (a target) which is inside the body and therefore invisible or almost invisible from the outside.

The invention aims in particular to simplify the positioning of equipment with respect to a support, and consequently with respect to a visible or invisible element inside the body of a subject.

Thus, the invention relates to a device for helping to position equipment with respect to a support, comprising a sheet of formable or thermoformable material configured to be attached to the support and comprising a guide for positioning the equipment.

Thus, it is proposed to use a sheet that is shaped to the surface of the support and further comprising a positioning device. As a result, not only is the equipment guided, therefore positioned correctly with respect to the sheet, but in addition, the sheet can take the exact shape of the support, thereby preventing the sheet from changing position with respect to the support.

This positioning helping device is particularly interesting when positioning equipment outside the body of a subject with respect to the position of a target object inside the body of the subject, and therefore with respect to a part of the surface of the body of the subject. It is thus possible, particularly advantageously, to simplify the positioning of equipment such as an activation tool of a distraction plate apparatus, outside the body of a subject, with respect to the distraction plate apparatus, inside the body of the subject, and thereby make this distraction plate apparatus easier to control.

The term "formable material" must be preferably interpreted in this case as being a rigid material having a first shape and capable of being shaped or modelled by simple shaping operations to obtain a second shape which will be kept, unless further shaping operations are performed. Such a material is for example plaster or a resin hardening in contact with the air.

The term "thermoformable material" must be preferably interpreted in this case as being a formable material as defined above and for which shaping operations involve changing the temperature of the material, for example by exposure to heat or immersion in a bath at a predefined temperature.

According to other optional characteristics of the positioning helping device, taken alone or in combination:

The positioning guide delimits a cavity of predetermined shape configured to position a part of the equipment to be positioned having a shape complementary to that of the cavity. The positioning of equipment whose shape is at least partially complementary to that of the cavity, is thereby optimised and efficient. The positioning of equipment with respect to the guide can therefore be predefined in all the positioning axes, in particular through the use of a shape acting as foolproofing system.

The cavity goes completely through the positioning guide. Equipment such as a magnetic, ultrasonic (Doppler) or ultrasound scan element can therefore be brought as close as possible to a target, such as a target of internal magnet type or an artery, for example, arranged behind the support, in particular inside the body of a subject on which the positioning helping device is placed.

The cavity of the guide is substantially cylindrical or substantially frustoconical. It is thus possible to align the longitudinal axes of the equipment (external) with equipment inside the subject on which the positioning helping device is placed, or to reproduce the correct positioning of external equipment with respect to an internal target, in other words to repeat the angular orientation planned between marked axes of the two items of equipment. For example, and if the target is a magnet inside the body, using a cylindrical cavity makes it possible to insert a neodymium cylindrical magnet magnetised perpendicular to its longitudinal axis and to align it coaxially with respect to the axis of a similar magnet of equipment inside a subject and with which it must be magnetically coupled. In addition, if the shape is frustoconical, a maximum distance from the target can be defined, depending on the equipment used.

The positioning guide is attached to the sheet of formable or thermoformable material by clipping, crimping, welding or bonding. The positioning helping device is therefore quick and easy to assemble. Assembly can be carried out during an operation to implant equipment in the body of a subject or at the same time as such an operation.

The cavity has a longitudinal axis forming an angle from 1 to 90 degrees with a plane comprising a base of the guide in contact with the sheet of formable or thermoformable material. The positioning of equipment can therefore be predefined along a predefined spatial orientation when this is required by equipment inside the subject so that it can be used or activated. For example, the rotation shaft of a neodymium magnet rotatably mounted in equipment implanted in the body of a subject may be oriented so that it is not perpendicular to the surface of the body of the subject at the intersection between the rotation shaft and the surface of the body.

The formable or thermoformable material is selected from a group comprising a thermoformable plate, plaster, papier-mâché, clay, resin or a material used for 3D printing. It is therefore easy to model, by converting it through the use of heat, or with water, depending on the material, without having to perform more complex operations.

The equipment positioning guide is made of a material selected from the group comprising PEEK (polyetheretherketone), polyurethane, titanium, stainless steel, gold, plaster, resin or glass. Advantageously, these materials are compatible to be placed in contact with the skin of a subject.

The device is designed for the positioning of equipment such as an activation tool for a distraction plate apparatus on a subject. The magnetic coupling can thus be optimised between a rotating magnet of the distraction plate apparatus and a rotating magnet of an activation tool for such a distraction plate apparatus, in order to optimise the magnetic coupling between these two items of equipment. In addition, this provides better control of a distraction plate apparatus inside a subject, with no need for transcutaneous access.

The sheet of formable or thermoformable material has at least partially the shape of a face. Advantageously therefore, the sheet of formable or thermoformable material can be shaped over the parts of a face likely to cover internal equipment such as, for example, a distraction plate apparatus for a maxillofacial application.

The invention also relates to a method for manufacturing a device for helping to position equipment comprising the steps of:
 increasing the temperature of a sheet of formable or thermoformable material,
 shaping the heated sheet of formable or thermoformable material by moulding on an object,
 perforating the sheet of formable or thermoformable material so as to form an opening, and
 attaching the equipment positioning guide in or opposite the opening, before or after the steps of increasing the temperature and shaping the sheet of material.

Such a method can be used to quickly manufacture a device for helping to position external equipment, for example during a surgical operation to implant equipment in a subject, or at the same time as such an operation. For example, a guide for helping to position an activation tool of a distraction plate apparatus can be manufactured during the operation to implant the distraction plate apparatus. Advantageously, and by implementing the method according to the invention, a practitioner (surgeon or nurse for example), can manufacture a device for helping to position equipment or a tool corresponding to the implantation, orientation or use characteristics of equipment implanted in the body of a subject.

FIGS. 10 to 16 show a device 10 for helping to position equipment according to a special and non-limiting embodiment of the invention.

FIG. 10 shows the device 10 for helping to position equipment on a support. The device 10 comprises a sheet 30 of formable or thermoformable material and a positioning guide 50 for helping to position equipment.

The guide 50 has a cavity 70, of cylindrical shape in this case. The cavity 70 may comprise an opening so that it opens onto a support (object or part of body) on which the device is applied.

At the top left of FIG. 10, the sheet 30 of formable or thermoformable material has not been previously shaped to adapt to a support. At the bottom right of FIG. 10, we see the device 10 after the sheet 30 of formable or thermoformable material has been shaped to adapt to a support. For example, the sheet 30 has been shaped on a lower part of the face of a subject, such as the bottom of a cheek, located near the chin, and opposite a part of the lower jaw of a subject.

The sheet 30 of formable or thermoformable material is made of thermoformable resin which can be shaped after increasing the temperature (hot water bath, for example). According to variants, the sheet 30 is made of a formable but not thermoformable material which can be modelled and keep its shape after modelling. For example, the sheet 30 of material may be a strip of plaster or an assembly of strips of plaster. According to other variants, the sheet 30 of material can be made of clay or of a material traditionally used for 3D printing (by a 3D printer). In this case, it is extremely important that the material should comply with the standards imposed for use when the sheet of material is in contact with the skin. These examples of materials are not limiting.

The guide 50 is preferably made of a rigid material, such as, for example PEEK, polyurethane, titanium, stainless steel, gold, plaster, resin, glass or a material traditionally used for 3D printing in compliance with the standards imposed for use when the sheet of material is in contact with the skin, this list not being exhaustive.

The sheet 30 of material, also called the "surface part" of the positioning helping device 10 may, according to a variant, have no opening opposite the guide 50 (in other words at the place where the guide 50 is positioned on the sheet 30). The guide 50 is also usually called the "volume part".

By providing the possibility of shaping the sheet 30 of material to any support, the device according to the invention can advantageously be used to adapt, with excellent precision, operations to the morphology of a subject or to the topology of a boundary surface delimiting the inside and the outside of an object.

The operations thus made possible or easier include for example medical or paramedical acts performed on a person and relating to a target element inside the body of this person.

The element to which an operation relates can be previously introduced into the body of the person concerned or be biologically or structurally part of the body of the person. For example, the internal element to which an act must relate is a distraction plate apparatus used to perform a bone expansion or an artery or a vein to be observed in a subject. For example, the internal element is a distraction plate apparatus, for example as described previously.

The device according to the invention can be used to optimise a fixed positioning of an object to be guided, outside the body of a patient, for an interaction with an object inside the body of a patient.

The device according to the invention thus considerably simplifies monitoring, measurement, activation or injection acts, these examples not being limiting.

For example, the device according to the invention can be used to position a Doppler effect probe opposite a vessel (artery or vein), along an axis imposed by the orientation of this artery in the body of a patient, and at a predefined distance from it. The device can also be used to position medical imaging equipment such as ultrasound scan equipment and more generally any device requiring precise positioning with respect to the body of a subject to ensure correct implementation of the operations to be performed.

A sensitive part of a vessel (artery or vein) can thus be monitored after undergoing a surgical operation, and after a practitioner has been able to manufacture the positioning helping device according to the invention during the surgical operation or at the same time as this operation.

Other acts can be simplified through the use of the device according to the invention allowing a predefined orientation of equipment with respect to a target object in the body of a patient, such as the insertion of a needle in a vessel, a tissue, a muscle, an organ, the positioning of a probe necessary to perform medical imaging acts, for example.

Advantageously and according to the planned use, the cavity 70 of the guide 50 may have different shapes.

For example, the cavity 70 may have a bore cross-section having a circular, triangular or quadrilateral shape or the shape of a polygon with more than 4 sides.

A machining cross-section of the cavity 70 of the guide 50 may correspond to remarkable triangles, a square, a rectangle or a diamond.

The cavity 7 may have a cylindrical volume, having a conical, parallelepipedic shape or any shape complementary to the shape of all or part of a tool or a probe.

Different openings may be provided between the inside and the outside of the cavity 70 of the guide 50, in particular to evacuate excess lubricant product used to introduce a tool or equipment more easily into the cavity 70. Such openings are then preferably oriented along an axis perpendicular to the longitudinal axis of the cavity 70.

According to an embodiment of the invention, the guide 50 consists of two parts 50A and 50B respectively called the upper half-guide and the lower half-guide.

FIG. 11 is an exploded view of a guide 50 for the device 10 according to the invention before assembly. The upper half-guide 50A comprises projecting pins configured for forced coupling, by insertion, in complementary cavities in the lower half-guide 50B. The lower half-guide 50B has a cylindrical base and a narrower open hollow trunk, also cylindrical, forming a cavity, and extending along a longitudinal axis from the base.

When the upper half-guide 50A, also provided with a base, is forcibly inserted into the lower half-guide 50B, the two bases are configured to clamp the sheet 30 of formable or thermoformable material between their respective surfaces.

The guide shown on FIG. 11 is such that the longitudinal axis of the cavity is perpendicular to the surface of the bases, and therefore to the surface of the sheet 30 of material, at the position where the guide 50 is inserted.

According to a first variant, shown on FIG. 12, the upper half-guide 50A is configured such that the longitudinal axis of the cavity of the guide is inclined at an angle of 15 degrees relative to the plane of its base.

The cavity thus oriented is used to guide a positioning of equipment at an angle of 15 degrees relative to the surface of the sheet 30 of material, at the location of the guide 50.

According to a second variant, shown on FIG. 13, the upper half-guide 50A is configured such that the longitudinal axis of the cavity of the guide is inclined at an angle of 30 degrees relative to the plane of its base.

The cavity thus oriented is used to guide a positioning of equipment at an angle of 30 degrees relative to the surface of the sheet 30 of material, at the location of the guide 50.

According to a variant of the embodiment of the invention, the upper half-guide 50A can be assembled on the lower half-guide 50B by bonding or welding so as to form a rigid assembly comprising the half-guides 50A and 50B and the sheet 30 of material around the bases.

According to another variant, and if the assembly is made by bonding or welding, the guide 50 may only consist of the upper half-guide 50A and use of the lower half-guide 50B is not necessary. In this case, the half-guide 50A may have no pins.

FIG. 14 illustrates a use of a device 10 according to the invention, for the positioning of an activation tool 9 of a distraction plate apparatus 80 positioned on the lower jaw of a subject 1000 to perform a maxillofacial bone expansion. The distraction plate apparatus 80 comprises a shaft bearing at its end a permanent rotating magnet magnetised perpendicular to its rotation shaft and whose rotation separates the plates to perform a bone expansion, through the use of a worm screw system.

The sheet 30 of the device 10 has been modelled on the face prior to the bone distraction operation to be performed, such as, for example, during the surgical operation to implant the distraction plate apparatus 80 in the body of the subject 1000, or shortly after this operation by a person knowing the characteristics required to implant the distraction plate apparatus (dimensions, orientation).

When shaping and assembling the device 10, the sheet 30 has been perforated to make an opening and the guide 50 has been assembled and/or positioned on this opening such that the cavity of the guide 50 allows precise guiding and at a predefined distance from a magnetic element required to activate the distraction plate apparatus 80 by magnetic coupling through the tissues of the subject 1000.

The activation tool 9 shown on FIG. 14 is configured to activate the distraction plate apparatus 80 by rotating the internal magnet of the distraction plate apparatus. The activation tool 9 therefore has a body 90 allowing it to be gripped. The body 90 of the tool 9 comprises a direct current motor 91 and a rotation shaft 92 solidly attached to the rotation shaft of the motor 91, bearing at its end a permanent magnet 93 magnetised perpendicular to its rotation shaft. The tool 9 comprises a control module 94 for controlling the direction and speed of rotation of the motor 91 using a 3-position switch 942. The positions of the switch 942 correspond respectively to a rotation of the motor in a first direction, a position in which the motor is stopped and a rotation of the motor in a second direction opposite to the first direction.

The device 10 for helping to position equipment can be used advantageously to align the rotation shafts of the magnet of the tool 9 and the magnet of the distraction plate apparatus 80, and to define an optimum distance between the two magnets to optimise the magnetic coupling and therefore the control of the distraction plate apparatus 80.

Advantageously, the cavity 70 of the guide 50 configured to introduce the magnet 93 of the tool 9 may comprise a stop, consisting for example of a collar inside the cavity of the guide 50, to prevent the magnet 93 from rubbing on the skin of the subject 1000. The same stop function can be achieved by the sheet 30 of material, if it is not provided with an opening opposite the cavity.

FIG. 15 illustrates an assembly of a guide 50 oriented at an angle of 15 degrees relative to a perpendicular of a sheet 30 at the location receiving the guide 50 to form a device 10, before shaping the sheet 30 on a support, such as the lower jaw of a person, for example.

The device 10 according to the invention may be supplied ready for use in various versions comprising a large variety of shapes of the guide 50. Thus, a practitioner, such as for example a surgeon or a nurse, can prepare the positioning helping device by selecting a model in a range suitable for the purpose and by modelling the sheet of formable or thermoformable material of the model selected on the body of a subject. The device 10 thus prepared will be adapted for future medical or paramedical acts. These acts will therefore be simplified, in particular for a person not used to or not specifically trained to perform them (medical imaging, injection, activation acts, for example).

A device 10 according to the invention may also be completely assembled during a medical act by successively increasing the temperature of the sheet 30 of formable or thermoformable material, shaping the heated sheet 30 of formable or thermoformable material by moulding on an object or a part of a body, perforating the sheet 30 of formable or thermoformable material so as to form an opening, and attaching the equipment positioning guide 50 in or opposite the opening made in the sheet 30. According to a variant, the guide 50 can be attached to the sheet 30 before shaping it.

Advantageously, and to adapt more closely to predefined shapes of objects or body parts, the sheet 30 of formable or thermoformable material may have different thicknesses or geometries.

Thus, the sheet 30 may have a triangular, quadrilateral, polygonal, circular or oval shape or a shape comprising a central part from which one or more lateral parts extend (for example a central circle from which two strips extend).

FIG. 16 shows the positioning helping device of FIG. 14, into which, for example, the end 1200 of an activation tool of a distraction plate apparatus is inserted.

According to another example, the end 1200 is the end of a Doppler effect probe used to view an artery and the sheet 30 can be modelled on the neck of a person in order to view a part of an artery of the person using medical imaging means connected to the Doppler effect probe comprising the end 1200.

The equipment positioning helping device 10 according to the invention considerably simplifies various acts of external activation or periodic monitoring of a target such as an internal surgical device and/or a biological structure.

It simplifies the external activation of magnetic distraction plate apparatus, in particular in case of maxillofacial surgery, as well as in case of orthodontics, and allows in particular better control over mandibular distraction, maxillary distraction, posterior cranial vault distraction, symphyseal distraction, alveolar distraction, facial monobloc advancement, palatal expansion.

Such a device can also be used in acts on metacarpal areas of the body, for bone transport operations.

In case of monitoring and/or follow-up by medical imaging, the device according to the invention can be used for vascular imaging acts by Doppler technique, in particular for the postoperative follow-up of vascular suturing when making flaps, for the use of ultrasound screening, for example when monitoring the progress of certain diseases, such as cancer.

Advantageously, the guide 50 and the sheet 30 are provided with openings (perforations) adapted to evacuate a sound conduction gel to optimise medical imaging operations such as, for example, operations implementing equipment using Doppler technology.

In addition, it is possible to optimise acts related to skin expansion for injections by valve, transcutaneous implantable chambers, or medical injection in predefined locations, the guiding part 5 being used to guide a syringe needle.

Advantageously, the device according to the invention can also be used for aortic and/or mitral valve reconstruction operations, for postoperative follow-up of reconstruction operations, where applicable.

Apart from its medical applications, the device according to the invention is suitable for industrial applications such as, for example, applications relating to the electro-nuclear industry, electricity production in general, or relating to all applications requiring a regular non-invasive check of pipes (casting, iron and steel, chemical industry, for example).

For example, it simplifies checks using ultrasound or X-ray probes of welds on pipes or tanks, or the monitoring of cracks in structures.

This type of use is particularly advantageous for the shipbuilding industry.

In other words, the device 10 for helping to position equipment with respect to a support such as an object or a part of the body of a subject comprises the sheet 30 made of formable or thermoformable material and configured to be attached to a support and comprises the guide 50 for positioning the assembled equipment on the sheet 30.

The positioning guide 50 delimits the cavity 70 of predetermined shape configured to position a part of equipment having a shape complementary to that of the cavity 70. The cavity 70 of the positioning guide 50 may go completely through it, or not, depending on the variant.

The cavity 70 of the guide 50 can have any shape, for example it may be substantially cylindrical or substantially frustoconical.

The positioning guide 50 is attached to the sheet 30 of formable or thermoformable material by crimping, bonding or through the use of screws or cylindrical or conical pins.

The cavity 70 may have a longitudinal axis forming an angle of 30 to 90 degrees with a plane comprising a base of the guide in contact with the sheet of formable or thermoformable material, such as the base of the half-guide 50A or that of the half-guide 50B, or a plane defined by the shape of the surface of the sheet 30 in contact with the guide 50.

The formable or thermoformable material of the sheet 30 comprises a material selected from the group comprising a thermoformable plate, plaster, papier-mâché, clay, resin or a material used for 3D printing.

The equipment positioning guide 50 is made of a material selected from the group comprising PEEK, polyurethane, titanium, stainless steel, gold, plaster, resin or glass.

The device 10 according to the invention is configured to optimise the positioning of an activation tool for a distraction plate apparatus implanted on a subject.

The sheet 30 of formable or thermoformable material can be arranged in a version having at least partially the shape of a face.

The device 10 can be manufactured in successive steps comprising:
increasing the temperature of the sheet 30 of formable or thermoformable material,
shaping the heated sheet 30 of formable or thermoformable material by moulding on an object or a part of a body of a subject,
perforating the sheet 30 of formable or thermoformable material so as to form an opening, and
attaching the equipment positioning guide 50, which comprises the cavity 70, in or opposite the opening, before or after increasing the temperature and shaping the sheet 30 of formable or thermoformable material.

Obviously, the invention is not limited to the embodiments described above but also relates to any device comprising a sheet of formable or thermoformable material configured to be attached to a support such as an object or a part of the body of a subject and comprising a guide for positioning equipment to be positioned with respect to a target inside the object or the body.

The invention claimed is:

1. An assembly for a bone expansion, comprising:
a bone expansion apparatus, wherein the bone expansion apparatus is a distraction plate apparatus;
an activation tool for the bone expansion apparatus, wherein the activation tool includes a magnetic element solidly attached to a rotation shaft of the activation tool, the magnetic element being configured to interact coaxially with a remote magnetic element borne by the bone expansion apparatus, the activation tool further including an electric motor configured to cause the rotation shaft to rotate, and a control module controlling the rotation of the rotation shaft; and
a device to assist positioning of the magnetic element of the activation tool with respect to the magnetic element borne by the bone expansion apparatus,
wherein the device to assist positioning of the magnetic element of the activation tool includes a sheet of formable or thermoformable material configured to be attached to a subject and including a guide for positioning the magnetic element, wherein the formable or thermoformable material is a rigid material and is of a first shape and configured to be further shaped or modelled by a shaping operation to obtain a second shape which will be retained thereof unless further shaping operation is performed.

2. The assembly according to claim 1, wherein the control module is configured to control a direction of rotation of the rotation shaft.

3. The assembly according to claim 1, wherein the control module is configured to control a speed of rotation of the rotation shaft.

4. The assembly according to claim 1, wherein the control module comprises a device for counting a number of portions of revolution made during the rotation of the rotation shaft.

5. The assembly according to claim 4, wherein the control module comprises a device for stopping the rotation of the rotation shaft when the rotation shaft has rotated through a predetermined number of revolutions.

6. The assembly according to claim 5, wherein the control module comprises a device for programming a direction of rotation and a number of revolutions of the rotation shaft to be made in this direction of rotation.

7. The assembly according to claim 1, wherein the activation tool comprises a magnetic field sensor configured to measure a variation in a magnetic field emitted by the remote magnetic element borne by the bone expansion apparatus when the remote magnetic element is aligned along a longitudinal axis of the rotation shaft of the activation tool on a side of the magnetic element solidly attached to the rotation shaft.

8. The assembly according to claim 7, wherein the activation tool comprises a magnetic field measurement module configured to determine a rotation of the remote magnetic element of at least a predetermined number of revolutions about a separation axis of the bone expansion apparatus.

9. The assembly according to claim 1, wherein the magnetic element of the activation tool comprises a magnet or a set of electromagnetic coils configured to generate a rotating magnetic field oriented perpendicular to the rotation shaft.

* * * * *